(12) United States Patent
Zappini

(10) Patent No.: US 8,552,087 B2
(45) Date of Patent: Oct. 8, 2013

(54) DENTAL MATERIALS WITH A HIGH FLEXURAL MODULUS

(75) Inventor: Gianluca Zappini, Torbole sui Garda (IT)

(73) Assignee: Ivoclar Vivadent AG, Schaan, Liechtenstein (LI)

( * ) Notice: Subject to any disclaimer, the term of this patent is extended or adjusted under 35 U.S.C. 154(b) by 179 days.

(21) Appl. No.: 12/584,721

(22) Filed: Sep. 10, 2009

(65) Prior Publication Data

US 2010/0068679 A1    Mar. 18, 2010

(30) Foreign Application Priority Data

Sep. 15, 2008 (EP) ..................................... 08164324

(51) Int. Cl.
*A61K 6/08* (2006.01)
*A61C 5/00* (2006.01)

(52) U.S. Cl.
USPC .......................... 523/116; 433/225; 433/228.1

(58) Field of Classification Search
USPC ............................... 523/116; 433/225, 228.1
See application file for complete search history.

(56) References Cited

U.S. PATENT DOCUMENTS

| | | | |
|---|---|---|---|
| 3,066,112 A | 11/1962 | Bowen | |
| 4,978,640 A | 12/1990 | Kelly | |
| 5,192,815 A | 3/1993 | Okada et al. | |
| 5,304,586 A | 4/1994 | Hammesfahr et al. | |
| 5,708,051 A * | 1/1998 | Erdrich et al. | 523/116 |
| 5,710,194 A | 1/1998 | Hammesfahr et al. | |
| 5,847,025 A | 12/1998 | Moszner et al. | |
| 5,865,623 A | 2/1999 | Suh | |
| 6,395,803 B1 | 5/2002 | Angeletakis | |
| 6,620,861 B1 | 9/2003 | Nakatuka et al. | |
| 6,696,507 B2 | 2/2004 | Subelka et al. | |
| 6,709,271 B2 | 3/2004 | Yin et al. | |
| 6,837,712 B2 | 1/2005 | Qian et al. | |
| 2006/0058415 A1 * | 3/2006 | Arthur et al. | 523/116 |
| 2006/0058418 A1 * | 3/2006 | Brandenburg et al. | 523/116 |
| 2006/0258771 A1 * | 11/2006 | Anton et al. | 523/115 |

FOREIGN PATENT DOCUMENTS

| | | |
|---|---|---|
| CA | 1103388 A1 | 6/1981 |
| DE | 102007035734 | 3/2008 |
| JP | 58069805 | 4/1983 |
| JP | 61241303 | 10/1986 |
| JP | 63303906 | 12/1988 |
| JP | 01026506 | 1/1989 |

OTHER PUBLICATIONS

A brochure for ALUNABEADS/CB by Showa Denko of Japan, 2 pages, Downloaded on Jan. 14, 2013.*
http://www.worddiq.com/definition/Modulus_of_elasticity; Modulus of elasticity—Definition; pp. 1-3; Sep. 6, 2012.
J. M. Söderholm: 'Posterior Composite Resin Dental Restorative Materials', 1985, 3M Company pp. 139-159.
Ullmanns Encyclopedia of Technical Chemistry vol. 2, 1988.
G. Ott: 'Composite Filing Materials' Ivoclar Vivadent Report No. 5 1990.
K. Vogel: 'Ivoclar Vivadent Report No. 18', 2007 Article 'Filler Technology', pp. 18-28.
U. Salz: 'The filled tooth—a complex composite system' Ivoclar Vivadent Report No. 7 1992.

* cited by examiner

*Primary Examiner* — Tae H Yoon
(74) *Attorney, Agent, or Firm* — Ann M. Knab; Thad McMurray

(57) ABSTRACT

Low viscosity composites, with a flexural modulus of at least 18 GPa and a flexural strength of at least 90 MPa for filling dental root canals for fixing post or as a build-up material on post, are composed of aluminum oxide with a mean particle size of 1 to 50 μm in combination with at least one additional filler with a mean particle size of 0.5 to 5 μm and a monomer mixture. Also disclosed is a method for the preparation of tooth restorations.

3 Claims, No Drawings

DENTAL MATERIALS WITH A HIGH FLEXURAL MODULUS

BACKGROUND OF THE INVENTION

1. Field of the Invention

All documents cited in the present patent application are incorporated by reference in their entirety in the present disclosure.

The present invention relates to polymerizable dental materials with a high flexural modulus.

The present invention relates in particular to low viscosity composites with a flexural modulus of at least 18 GPa and a flexural strength of at least 90 MPa.

These composites comprise a first filler with a mean particle size of 1 to 50 μm in combination with at least one additional filler with a mean particle size of 0.5 to 5 μm and a monomer mixture. Aluminum oxide has emerged as a particularly preferred first filler.

2. Description of the Related Art

Polymerizable organic plastics for use as dental material have been known since the 1930s and the use of one of the most well known dental monomers (Bis-GMA) was in particular described in U.S. Pat. No. 3,066,112. Because of the mechanical properties of the polymers obtained, these cannot be used alone. An improvement in the properties can be obtained using fillers. A review of the development of such composites is given, inter alia, in K.-J. M. Soderholm, "Posterior Composite Resin Dental Restorative Materials", pp. 139-159, 3M Company, 1985; G. Ott, "Composit-Fullungsmaterialien" [Composite Filling Materials], Ivoclar Vivadent Report No. 5, 1990, U. Salz, "Der gefullte Zahn—ein komplexes Verbundsystem" [The Filled Tooth—A Complex Composite System], Ivoclar Vivadent Report No. 7, 1992, and K. Vogel, "Fullstofftechnologie" [Filler Technology], Vivadent Report No. 18, pp. 18-28, 2007.

The individual components can be chosen and combined depending on the use of the composite materials (composed of the main constituents monomer, filler and initiator for the polymerization). In recent years, in addition to the handling properties, the polymerization shrinkage and the mechanical properties, it is above all the aesthetics which have been to the fore in the development of composites. With regard to their viscosity, composites can be roughly subdivided into two groups: on the one hand into packable (high viscosity) composites and, on the other hand, into flowable (low viscosity) composites (flowables). Due to the higher proportion of monomer in the flowables, the mechanical properties achievable, in particular the flexural modulus, can more likely be assessed as poor; however, the viscosity is clearly lower than with the highly filled composites.

However, it has turned out that it can be more economical to prepare even composites for a rather limited field of application than is the case for the "universal composites".

In the repair of devitalized teeth, posts are frequently fixed in the roots and the dental crown is then built up on these. In order to be able to insert these posts, the root canals can be appropriately prepared, thus drilled and smoothed out. Due to the curvature of the root canals, a great deal of healthy material of the tooth is naturally lost during the drilling or the curvature of the root is allowed to remain and thinner or more flexible posts are inserted. With thin posts in particular, what now matters is that a composite can be made available for the fixing and for the build-up which exhibits the high mechanical strengths necessary and which can be satisfactorily applied in the thin root canals.

A number of documents are admittedly known from the state of the art, e.g. JP 1026506, JP 61241303, JP 63303906, JP 58069805, U.S. Pat. No. 6,709,271 B2, U.S. Pat. No. 6,837,712 B2, U.S. Pat. No. 6,696,507 B2, U.S. Pat. No. 6,620,861 B1, U.S. Pat. No. 6,395,803 B1, U.S. Pat. No. 5,865,623, U.S. Pat. No. 5,847,025, U.S. Pat. No. 5,710,194, U.S. Pat. No. 5,192,815 and U.S. Pat. No. 4,978,640, which describe the use of aluminum oxide as filler in dental composites or composites with good properties; however, nothing was disclosed in the state of the art which suggests the use of aluminum oxide particles in a particular particle size with simultaneous increase or maintenance of the mechanical strength values and comparatively low viscosity of the composites.

Root canal posts are used in endodontically treated nonvital teeth which exhibit extensive coronal damage. This type of therapy is known as postendodontic treatment.

In the past, it was assumed that, in endodontic treatment, the root canal posts strengthen the root canal structure, which has been pretreated. Nowadays, the root canal posts are used to make available a firm and reliable anchoring for the core build-up. A root canal post is necessary with severe destruction of the coronal tooth structure.

Until recently, root canal posts were still prepared from stainless steel or titanium. In view of the fact that more and more composites and ceramic materials are being used for core build-up, aesthetic considerations are exerting ever more influence over the choice of the post material. Dark metal posts are visible through the composites and translucent ceramic materials, resulting in the natural image of the restorations being spoilt. This has led to the introduction of posts which consist of ceramic or fiber-reinforced composites. Fiber-reinforced composites in particular are becoming more and more accepted.

Usually, the postendodontic procedure (direct restoration) consists of the following stages:

Preparation of the remaining coronal structure and removal of the root canal filling (gutta percha) with Gates, Peeso or Largo reamers Preparation and enlargement of the root canal up to the necessary depth using the corresponding drill Adjustment by means of testing of the endodontic post and, if necessary, shortening of the post Application of fixing composite to the post and insertion into the root canal and curing of the composite (light curing or self-curing)

Build-up of the core with a core build-up composite

One considerable disadvantage of this method is the enlargement of the root canal, for the danger exists of root perforation and weakening of the root structure. A method for postendodontic restoration which no longer includes this stage would eliminate the potential risks mentioned and it would furthermore be markedly more agreeable for the dentist and the patient. Ideally, such a new method would also shorten the handling time.

However, the problem in this connection is that, without enlargement of the root canal, preprepared endodontic posts would not be suitable if they do not exhibit a markedly smaller diameter.

A smaller diameter means, though, a poorer stiffness of the posts and accordingly of the entire reconstruction. A poorer stiffness would be detrimental to the stability of the crown, with the possible emergence of risks of separation or crack formation.

Theoretically, this lack of stiffness due to the smaller dimensions could be compensated for by increasing the flexural modulus of the material.

For example, a post with a diameter of 0.6 mm would be suitable in almost any root canal, whereas normal posts exhibit a diameter of between 1.0 and 2.0 mm. The reduction in the diameter from 1.0-2.0 mm down to 0.6 mm would demand a twofold to threefold increase in its flexural modulus, in order to achieve the same stiffness of the entire reconstruction (post plus core build-up). Conventional fiber-reinforced composite posts are based on glass or quartz fibers and exhibit a flexural modulus of approximately 40 GPa. This means that the material which is used for an appropriately thinner post must exhibit a flexural modulus of more than 80-120 GPa. According to the current state of the art in the field of fiber technology, such properties are, however, only achieved by carbon fibers, crystalline polymer fibers and ceramic fibers (SiC, $Al_2O_3$). Due to their colouring (black or yellow) and their high cost, these materials are not, however, attractive for this application. An additional possibility would be use of metal posts; however, these are unattractive and can set off allergies.

On the other hand, the stiffness of the reconstruction from post and core build-up is likewise determined through the core build-up material. Theoretically, the reduced stiffness of the post can be compensated for by increasing the flexural modulus of the fixing and core build-up material to 20 GPa or more.

Normally, build-up composites exhibit a flexural modulus of 6 to 15 GPa; however, the fixing materials exhibit a flexural modulus only in the range from 3 to 8 GPa. Admittedly, there already exist some dental composites with flexural modulus values of 18 GPa or more; however, these exhibit an excessively high consistency and cannot be used as fixing material in the root canal.

To summarize, dental composites are known from the state of the art having a flexural modulus of up to 20 GPa. On the other hand, composites with low viscosities ("flowables") are also known. In this connection, it is also known that the composites with a high flexural modulus always exhibit a high viscosity (depth of penetration of less than 1 mm). In contrast, flowables have a low viscosity (depth of penetration from 5 to 20 mm); however, the flexural modulus here is only in the region of less than 10 GPa.

Low viscosity composites with simultaneously a high flexural modulus are not known from the state of the art.

It would thus be desirable to have available a dental composite which exhibits a flexural modulus of more than 20 GPa and simultaneously a consistency which allows it to be used as endodontic fixing material, thus exhibits a depth of penetration of more than 5 mm, which can also simultaneously be used as core build-up composite.

SUMMARY OF THE INVENTION

The object of the present invention is accordingly that of providing dental composites which do not exhibit the above-mentioned disadvantages. The object of the present invention is in particular that of providing dental composites which exhibit a high flexural modulus and simultaneously have good flow properties.

These dental composites are to be usable both as core build-up composites and as fixing materials.

This object is achieved through low viscosity composites exhibiting a flexural modulus of at least 18 GPa and a flexural strength of at least 90 MPa which comprise a first filler with a mean particle size of 1 to 50 μm in combination with at least one additional filler with a mean particle size of 0.5 to 5 μm and a monomer mixture.

The depth of penetration is determined in the context of the present invention by following ASTM D 1321 ("Standard Test Method for Needle Penetration of Petroleum Waxes"), use being made of a penetrometer PNR 10 and of a flat-head cylinder with a diameter of 4 mm and a weight of 17.6 g. After a measurement time of one second, the penetration (depth of penetration) is measured.

In the context of this invention, high viscosity composites is understood to mean those with a depth of penetration of less than 1 mm, medium viscosity composites is understood to mean those with a depth of penetration of from 1 to 5 mm and low viscosity composites is understood to mean those with a depth of penetration of greater than 5 mm.

The "low viscosity" and "good flow properties" properties are used synonymously in the invention; the assigning takes place in this connection according to the above assigning of the composites with regard to the depth of penetration, determined by means of a penetrometer.

The terms flexural modulus or flexural strength are to be understood as meaning the material properties defined according to DIN EN ISO 178 ("Plastics—Determination of flexural properties"); the measurement is carried out in this connection according to dental standard ISO 4049 ("Dentistry—Polymer-based filling, restorative and luting materials"). In this described measurement, both material properties are simultaneously measured and also indicated.

The particle size can in the context of the present invention be determined according to different methods; these are, inter alia, described in detail in Ullmann's Encyclopedia of Industrial Chemistry, volume 2 (1988), Unit Operations, e.g. air separation, classification, flotation, electrostatic or also magnetic separation methods. In the size range relevant to the present invention, the results of the individual methods are comparable, so that the different determination methods are to be regarded as equivalent in the context of the present invention.

In the context of the present invention, all figures for amounts, unless otherwise indicated, are to be understood as figures by weight.

In the context of the present invention, the term "ambient temperature" means a temperature of 23° C. Figures for temperatures are, unless otherwise indicated, always in degrees Celsius (° C.).

Unless otherwise indicated, the reactions or processing stages referred to are carried out at standard pressure (atmospheric pressure).

In the context of the present invention, the term "photoinitiator" is understood to mean, unless otherwise indicated, both photosensitizers and photoinitiators in the narrower sense.

In the context of the present invention, the term "composites" includes physical and/or chemical mixtures or combinations of monomers, polymers, copolymers or mixtures of monomers, polymers or copolymers with at least 10% by weight of one or more inorganic substances. Inorganic substances which may be present are preferably pigments and fillers.

The expression (meth)acryloyl is to include, in the context of the present invention, both methacryloyl and acryloyl or mixtures of the two.

The various features of novelty which characterize the invention are pointed out with particularity in the claims annexed to and forming a part of the disclosure.

DETAILED DESCRIPTION OF THE INVENTION

In the context of the present invention, it has surprisingly been found that the combination of well-chosen fillers and specific monomers makes possible the preparation of composites exhibiting a high flexural modulus and simultaneously a lower viscosity, so that they can be used as core build-up material and as fixing composite.

Accordingly, a subject matter of the present invention is low viscosity composites exhibiting a flexural modulus of at least 18 GPa and a flexural strength of at least 90 MPa which comprise a first filler with a mean particle size of 1 to 50 μm combination with at least one additional filler with a mean particle size of 0.5 to 5 μm and a monomer mixture. In the context of the present invention, aluminum oxide has proven to be particularly preferred as first filler.

The first essential element of the composites according to the invention is the first filler, in particular aluminum oxide, with a mean particle size of 1 to 50 μm, preferably 5 to 40 μm, particularly preferably 10 to 25 μm.

In this connection, use may be made, for example, of commercial aluminum oxides, such as those available, e.g., under the names MKE Edelkorund weiss (Eisenwerk Würth GmbH, D-Bad Friedrichshall), Martoxid (Martinswerk GmbH, D-Bergheim) or Almatis Alumina (Almatis GmbH, D-67065 Ludwigshafen). The aluminum oxides can be spherical or can also have other shapes. They are preferably produced by milling and are thus nonspherical.

The aluminum oxides can, in a preferred embodiment of the present invention, be surface-modified. On the one hand, this guarantees good integration in the polymer base and, on the other hand, this results in a low viscosity and a high flexural strength.

Surface modification can be carried out, according to the state of the art, with silanes, with anhydrides, with (meth)acrylate groups or, preferably, with radically polymerizable monomers which have acid groups. Phosphate, phosphonic acid, sulphonic acid and/or carboxylic acid groups are preferred as acid groups of the monomers. Particular preference is given to surface modification with methacrylates comprising phosphate groups and very particular preference is given to surface modification with methacryloyloxydecyl dihydrogen phosphate.

The aluminum oxide described above is combined according to the invention with at least one additional filler with a mean particle size of 0.5 to 10 μm, in particular 0.5 to 2 μm.

The fillers conventional in dental technology, such as glass or glass ceramic fillers, quartz, composite fillers or pyrogenic silicas, are suitable as additional fillers. In this connection, the additional filler can also be an aluminum oxide or an additional metal oxide (such as, e.g., titanium oxide or zirconium oxide), though with appropriately lower mean particle sizes.

Preference is given to the use of a surface-modified glass filler as additional filler, the surface modification preferably being carried out via silanes. Use may be made, for this, of standard commercially available silanizing agents, such as vinyltriethoxysilane, vinyltrimethoxysilane, vinyltris(2-methoxyethoxy)silane, g-methacryloyloxypropyltrimethoxysilane (silane A-174), g-methacryloyloxypropyltris (2-methoxyethoxy)silane, g-glycidoxypropyltrimethoxysilane, vinyltriacetoxysilane, g-mercaptopropyltrimethoxysilane, g-aminopropyltriethoxysilane or N-(b-aminoethyl)-g-aminopropyltrimethoxysilane (Union Carbide). The A-174 is particularly preferred in this connection.

As an alternative to aluminum oxide, use may be made of additional first fillers, the criterion for which is that they exhibit an elastic modulus of more than 200 GPa. Examples of this are, e.g., $ZrO_2$ and $TiO_2$ and standard carbides, diborides or nitrides, such as TaC, TiC, WC, ZrC, VC, NbC, SiC, $B_4C_3$, $TiB_2$, $ZrB_2$, $MgB_2$, $Si_3N_4$, TiN or AlN.

In a preferred alternative form, X-ray-opaque fillers are additionally added. Use is preferably made, as X-ray-opaque fillers, of oxides and salts of heavy metals; the X-ray-opaque fillers are particularly preferably chosen from the group consisting of ytterbium trifluoride, nanoparticulate tantalum(V) oxide, barium sulphate, bismuth oxide and mixtures thereof. $YbF_3$ is particularly preferred.

All monomers conventional in dental technology, in particular the radically polymerizable mono- and polyfunctional (meth)acrylates, are suitable as monomers for use in the monomer mixture of the present invention. Use may be made, as radically polymerizable monomers, of mono- or polyfunctional (meth)acrylates or (meth)acrylamides ((meth)acryloyl compounds). Monofunctional (meth)acryloyl compounds is to be understood as meaning compounds with one (meth)acryloyl group and polyfunctional (meth)acryloyl compounds is understood to mean compounds with two or more, preferably from 2 to 3 (meth)acryloyl groups. Polyfunctional monomers have crosslinking properties.

Preferred monofunctional (meth)acryloyl compounds are commercially available monofunctional monomers, such as methyl, ethyl, butyl, benzyl, furfuryl or phenyl (meth)acrylate, and also 2-hydroxyethyl or 2-hydroxypropyl (meth)acrylate.

Preferred polyfunctional (meth)acryloyl compounds are bisphenol A di(meth)acrylate, Bis-GMA (an addition product of methacrylic acid and bisphenol A diglycidyl ether), ethoxylated bisphenol A di(meth)acrylate, UDMA (an addition product of 2-hydroxyethyl methacrylate and 2,2,4-trimethylhexamethylene diisocyanate), di-, tri- or tetraethylene glycol di(meth)acrylate, trimethylolpropane tri(meth)acrylate, pentaerythritol tetra(meth)acrylate, and also butanediol di(meth)acrylate, 1,10-decanediol di(meth)acrylate or 1,12-dodecanediol di(meth)acrylate, crosslinking pyrrolidones, such as, e.g., 1,6-bis(3-vinyl-2-pyrrolidonyl)hexane, or commercially available bisacrylamides, such as methylene- or ethylenebisacrylamide, or bis(meth)acrylamides, such as, e.g., N,N'-diethyl-1,3-bis(acrylamido)propane, 1,3-bis (methacrylamido)propane, 1,4-bis(acrylamido)butane or 1,4-bis(acryloyl)piperazine, which can be synthesized by reaction of the corresponding diamines with (meth)acryloyl chloride.

Use may furthermore be made of hydrolysis-resistant monomers, such as hydrolysis-resistant mono(meth)acrylates, e.g. mesityl methacrylate, or 2-(alkoxymethyl)acrylic acids, e.g. 2-(ethoxymethyl)acrylic acid, 2-(hydroxymethyl) acrylic acid, N-monosubstituted or N,N-disubstituted acrylamides, such as, e.g., N-ethylacrylamide, N,N-dimethylacrylamide, N-(2-hydroxyethyl)acrylamide or N-methyl-N-(2-hydroxyethyl)acrylamide, and N-monosubstituted methacrylamides, such as, e.g., N-ethylmethacrylamide or N-(2-hydroxyethyl)methacrylamide, and also in addition N-vinylpyrrolidone and allyl ether. These monomers are liquid at ambient temperature and are accordingly also suitable as (reactive) diluent.

Use may likewise be made of radically polymerizable monomers comprising acid groups. Carboxylic acid groups, phosphonic acid groups, phosphate groups and/or sulphonic acid groups are preferred acid groups, it being possible for these groups to be present in the acid form, as anhydride or in the form of an ester. Preference is given in this connection to monomers with phosphonic acid groups or phosphate groups. The monomers can exhibit one or more acid groups; preference is given to compounds with from 1 to 2 acid groups.

Maleic acid, acrylic acid, methacrylic acid, 2-(hydroxymethyl)acrylic acid, 4-(meth)acryloyloxy-ethyltrimellitic acid or the corresponding anhydride, 10-methacryloyloxydecylmalonic acid, N-(2-hydroxy-3-(methacryloyloxy)propyl)-N-phenylglycine, N-acryloyl-a-aspartic acid (AAA) and 4-vinylbenzoic acid are preferred polymerizable carboxylic acids.

Vinylphosphonic acid, 4-vinylphenylphosphonic acid, 4-vinylbenzylphosphonic acid, 2-methacryloyloxyethylphosphonic acid, 2-methacrylamidoethylphosphonic acid, 4-methacrylamido-4-methylpentylphosphonic acid, 2-[4-(dihydroxyphosphoryl)-2-oxabutyl]acrylic acid, 2-[2-(dihydroxyphosphoryl)ethoxymethyl]acrylic acid 2,4,6-trimethylphenyl ester and 2-[2-(dihydroxyphosphoryl)-ethoxymethyl]acrylic acid ethyl ester (DPEAE) are preferred phosphonic acid monomers. 2-Methacryloyloxypropyl monohydrogen and dihydrogen phosphate, 2-methacryloyloxyethyl monohydrogen and dihydrogen phosphate, 2-methacryloyloxyethyl phenyl hydrogen phosphate, dipentaerythritol pentamethacrylate phosphate, 10-methacryloyloxydecyl dihydrogen phosphate (MDP), phosphoric acid mono(1-acryloylpiperidin-4-yl) ester, 6-(methacrylamido)hexyl dihydrogen phosphate, 1,3-bis(N-acryloyl-N-propylamino)propan-2-yl dihydrogen phosphate and 1,3-bis(methacrylamido)propan-2-yl dihydrogen phosphate (BMPP) are preferred acidic polymerizable phosphoric acid esters.

Vinylsulphonic acid, 4-vinylphenylsulphonic acid or 3-(methacrylamido)propylsulphonic acid are preferred polymerizable sulphonic acids.

Use may also be made, as mono- or polyfunctional monomer, of polymerizable compounds exhibiting an antimicrobial action, such as, e.g., 12-methacryloyloxydodecylpyridinium bromide; particular preference is given to "macromers" comprising a polymeric spacer between the polymerizable group and the group with the antimicrobial action.

Use may likewise be made of specific monomers, such as, e.g., the polymerizable calix[n]arenes described in DE 10 2007 035 734 A1 in sections [0021] and [0022].

Particularly good results are obtained if the monomers of the monomer mixture are chosen from two or more monomers from the group consisting of urethane di(meth)acrylate, ethoxylated bisphenol A di(meth)acrylate, ditrimethylolpropane tetra(meth)acrylate, decanediol di(meth)acrylate, tricyclodecanedimethanol di(meth)acrylate, tetrahydrofurfuryl (meth)acrylate, hydroxyethyl(meth)acrylate, dimethyl(meth)acrylamide and dimethylaminoethyl(meth)acrylate, it being preferable to choose the monomers from the group consisting of urethane dimethacrylate, ethoxylated bisphenol A dimethacrylate, ditrimethylolpropane tetraacrylate, decanediol dimethacrylate, tricyclodecanedimethanol dimethacrylate, tetrahydrofurfuryl methacrylate, hydroxyethyl methacrylate, dimethylacrylamide and dimethylaminoethyl methacrylate.

In an especially preferred alternative form of the present invention, between 5 and 30% by weight, preferably between 10 and 25% by weight, of hydrolysis-resistant (meth)acrylamides and/or amino (meth)acrylates are present as reactive liquefiers (reactive diluents) in the monomer mixture, in particular if this consists of monomers from the groups just mentioned.

In the context of the present invention, the standard initiators for light curing and self-curing are used for the radical polymerization. In this connection, self-curing and dual curing are preferred as type of polymerization; however, pure light curing (photopolymerization) is also possible.

With light curing (photopolymerization), the curing is initiated by radical formation of the photoinitiators themselves (Norrish type I) or with the additional use of coinitiators (Norrish type II).

Self-curing is understood to mean, in the context of the present invention, that the curing takes place spontaneously, without an additional supply of energy (such as light or heat). Use is always made here of combinations of initiators and activators or the well known redox systems.

Dual curing is understood to mean, in the context of the present invention, a combination of self-curing and light curing.

These interrelations are known to a person skilled in the art; however, the following section should promote a better understanding thereof.

With self-curing, the polymerization is started without an external supply of energy. The polymerization is started using systems of activators (reducing agents) and catalysts/initiators (oxidizing agents), also known as redox systems, which are located separately in two components of the filling material; on mixing together the two, the reaction is set underway.

In the context of the present invention, the redox systems which can be used for the self-curing are based on an oxidizing agent, in particular peroxide or hydroperoxide, and a reducing agent. In the context of the present invention, all standard redox systems with the known oxidizing agents and reducing agents can in principle be used.

Oxidizing agents which can be satisfactorily used according to the invention are cobalt(III) chloride, tert-butyl hydroperoxide, iron(III) chloride, perboric acid and its salts and salts with permanganate or persulphate anions and in particular dibenzoyl peroxide or dilauryl peroxide, most preferably dibenzoyl peroxide.

Reducing agents which can be used according to the invention are cobalt(II) chloride, iron(II) chloride, iron(II) sulphate, hydrazine, oxalic acid, thiourea and salts with dithionite or sulphate anions.

Reducing agents which can be particularly satisfactorily used according to the invention are tertiary aromatic amines, such as, e.g., N,N-diethanol-p-toluidine, N,N-dimethyl-p-toluidine, N,N-dihydroxyethyl-p-toluidine, N,N-diethyl-3,5-di(tert-butyl)aniline or N,N-dimethyl-sym-xylidine, ascorbic acid, p-toluenesulphinic acid or trimethylbarbituric acid, in particular N,N-dimethyl-p-toluidine, N,N-dimethyl-sym-xylidine and diethyl-3,5-di(tert-butyl)aniline.

Use is particularly preferably made, in the context of the present invention, for the self-curing, of benzoyl peroxide or diethyl-3,5-di(tert-butyl)aniline.

Suitable photoinitiators are, e.g., dibenzoyldiethyl-germanium, dibenzoyldimethylgermanium, benzophenone, benzoin and also derivatives, in particular benzoin ethers, dialkyl benzil ketals, dialkoxyacetophenones, acylphosphine or bisacylphosphine oxides, a-diketones or the derivatives thereof, such as 9,10-phenanthrenequinone, diacetyl, furil, anisil, 4,4'-dichlorobenzil and 4,4'-dialkoxybenzil, 2,2-dimethoxy-2-phenylacetophenone and camphorquinone.

In the context of the present invention, camphorquinone is preferably used as photoinitiator. Ethyl 4-dimethylaminobenzoate (EMBO) is preferably used as coinitiator for the light curing.

In the context of the present invention, however, use may also be made, as photoinitiators, of all other conventional photoinitiators, optionally also in combination with one another.

Examples of particularly suitable photoinitiators are, in addition to camphorquinone and EMBO, inter alia, the acylphosphine oxides, in particular 2,4,6-trimethyl-benzoyl-diphenylphosphine oxide (Lucirin TPO) or bis(2,6-dichlorobenzoyl)(4-(n-propyl)phenyl)phosphine oxide.

Finally, additional additives can be added, if necessary, to the composites according to the invention, such as, e.g., stabilizers, UV absorbers, flavouring agents, additives which give off fluoride ions, optical brighteners, plasticizers, dyes or pigments.

A preferred UV absorber in this connection is 2-hydroxy-4-methoxybenzophenone; preferred stabilizers are 2,6-di (tert-butyl)-4-cresol and 4-methoxyphenol.

If the composites according to the invention are to be cured by self-curing or dual curing, the constituents are divided into a base paste and a catalyst paste, preferably in the ratio by volume of 1:1. For this, a starting paste is made up from the monomer mixture and the fillers and is then divided into equal parts. The oxidizing agent, optionally together with a stabilizer, is then added to the first part, the catalyst paste; the reducing agent and, for the case of the dual curing, the photoinitiator are added to the second part, the base paste.

In a preferred alternative form of the present invention, the low viscosity composites consist of from 10 to 40% by weight of monomer mixture from 40 to 70% by weight of aluminum oxide with a mean particle size of 1 to 50 μm from 10 to 45% by weight of at least one additional filler with a mean particle size of 0.5 to 5 μm and from 0.001 to 3% by weight of initiators and additional additives, the percentages adding up to 100% by weight.

The composites according to the invention exhibit thixotropic properties, i.e. they reversibly reduce their viscosity under the action of forces; after the end of the action of the force, they again exhibit the original viscosity. They show a low viscosity, i.e. a depth of penetration of more than 5 mm, measured with the penetration method. The composites according to the invention exhibit a flexural modulus of greater than 18 GPa. It is preferable for them to exhibit a flexural modulus of 18 to 30 GPa, preferably of 20 to 25 GPa. In this connection, they simultaneously exhibit a flexural strength of 90 to 300 MPa, preferably of 100 to 180 MPa.

Because of the thixotropic properties of the composites according to the invention, i.e. a reduction in viscosity at high shear forces, such as, e.g., when ejecting from nozzles, a narrow root canal can be very easily filled, into which a post, e.g. of metal, ceramic or fiber-reinforced composite, is then inserted and, by curing the composite, fixed. Due to the high flexural modulus of the composites according to the invention, a stable build-up, which is used to support the crown, is guaranteed.

The composites of the present invention are suitable in particular for the use
a) as filling of tooth root canals for the fixing of posts,
b) as build-up material, e.g. on posts.

The composites according to the invention exhibit a number of advantages, the most important of which are as follows:

the composite can be used both for the fixing of posts and for the construction of the build-up—one product, instead of, as hitherto, two products, the stability of the build-up is also guaranteed when very thin posts are used; it is not necessary to enlarge the root canal using a drill; the treatment is more sparing of the tooth substance and the risk of root perforation due to drilling mistakes is lower than with previous methods.

Another subject matter of the present invention is a method for tooth restoration which comprises the following stages:
a) preparation of the remaining coronal structure and removal of the root canal filling (gutta percha) with Gates, Peeso or Largo reamers,
b) preparation of the root canal up to the necessary depth using the corresponding drill,
c) adjustment by means of testing of the endodontic post,
d) if necessary, shortening of the post,
characterized in that a composite according to the present invention is used.

Due to the outstanding profile of properties, the composites according to the invention are also suitable for use in other fields than dentistry.

In an alternative form of the present invention, the composites are free from polypropylene glycol dimethacrylates or polytetramethylene glycol dimethacrylates.

The various embodiments of the present invention, e.g. those of the various dependent claims, can in this connection be combined with one another in any way.

The invention is now explained with reference to the following nonlimiting examples.

The following abbreviations are used in the examples:

| Abbreviation | Meaning |
|---|---|
| V380 | Urethane dimethacrylate |
| SR348C | Ethoxylated bisphenol A dimethacrylate |
| SR355 | Ditrimethylolpropane tetraacrylate |
| D3MA | Decanediol dimethacrylate |
| DCP | Tricyclodecanedimethanol dimethacrylate |
| THFMA | Tetrahydrofurfuryl methacrylate |
| HEMA | Hydroxyethyl methacrylate |
| N,N-DMAA | Dimethylacrylamide |
| DMA-EMA | Dimethylaminoethyl methacrylate |
| MDP | Methacryloyloxydecyl dihydrogen phosphate |
| A-174 | g-Methacryloyloxypropyltrimethoxysilane |
| F360 | High-grade corundum powder ($Al_2O_3$, 12-40 μm) |
| F1000 | High-grade corundum powder ($Al_2O_3$, 1-10 μm) |
| GM27884 | Barium glass powder (mean particle size 1 μm) |
| YbF3 | Ytterbium trifluoride powder (mean particle size 0.1 mm) |
| CC | Camphorquinone |
| EPD or EMBO | Ethyl p-dimethylaminobenzoate |
| DABA | Diethyl-3,5-di(tert-butyl)aniline |
| BPO | Benzoyl peroxide |
| BHT | Di(tert-butyl)-p-cresol |

Examples 1 to 6

The following compositions were used for Examples 1 to 6, the numerical values representing % by weight. The composites are prepared by intensively mixing, e.g. on a kneader, subsequently degassing and drawing the product off into suitable primary packagings (syringes or cavifills).

| | % by weight | | | | | |
|---|---|---|---|---|---|---|
| | 1 | 2 | 3 | 4 | 5 | 6 |
| V380 | 5.0 | 5.2 | 5.1 | 5.6 | — | — |
| SR348C | 4.6 | — | 4.5 | 5.0 | 3.9 | 5.0 |
| SR355 | — | 3.0 | — | — | — | — |
| D3MA | — | 2.2 | — | — | — | — |
| DCP | — | — | — | — | 4.9 | 6.2 |
| THFMA | 2.0 | — | 2.0 | 2.3 | — | — |
| HEMA | 0.6 | 1.8 | 0.6 | 0.6 | 1.0 | 1.2 |
| N,N-DMAA | 1.6 | 1.7 | — | 1.7 | — | — |
| DMA-EMA | — | — | 1.6 | — | 2.8 | 1.2 |
| MDP | 1.0 | 0.9 | 1.1 | 0.9 | 0.8 | — |
| A-174 | — | — | — | — | — | 2.1 |
| F360 | 56.6 | 48.1 | 56.5 | 40.3 | 55.6 | 50.1 |
| F1000 | 6.9 | 16.8 | 6.9 | 17.2 | 5.5 | — |
| GM27884 | 21.6 | 20.2 | 21.6 | 26.3 | 25.4 | 17.0 |
| YbF3 | — | — | — | — | — | 17.1 |

-continued

| | % by weight | | | | | |
|---|---|---|---|---|---|---|
| | 1 | 2 | 3 | 4 | 5 | 6 |
| CC | 0.05 | 0.05 | 0.05 | 0.05 | 0.05 | 0.05 |
| EPD | 0.05 | 0.05 | 0.05 | 0.05 | 0.05 | 0.05 |
| Total | 100 | 100 | 100 | 100 | 100 | 100 |

Physical properties of the compositions according to Examples 1 to 6 in comparison with compositions of the state of the art not comprising aluminum oxide fillers:

| | Description | Depth of penetration [mm]** | Flexural modulus [GPa]* | Flexural strength [MPa]* |
|---|---|---|---|---|
| Example 1 | Flowable | 5.2 | 24 | 148 |
| Example 2 | Flowable | 7.2 | 24 | 147 |
| Example 3 | Flowable | 6.3 | 21 | 124 |
| Example 4 | Flowable | 12.8 | 21 | 124 |
| Example 5 | Flowable | 8.5 | 22 | 100 |
| Example 6 | Flowable | 12.0 | 20.1 | 120 |
| Tetric Ceram | Highly viscous paste, filling composite | <0.1 | 10.0 | 120 |
| In Ten-S | Highly viscous paste, filling composite | <0.1 | 10.5 | 130 |
| Tetric EvoFlow | Flowable, filling composite | 6.7 | 5.1 | 114 |
| Variolink II | Flowable, fixing composite | 6.2 | 8.3 | 115 |
| Multicore HB | Highly viscous paste, core build-up material | <0.1 | 14-18 | 125-140 |
| Multicore Flow | Flowable, core build-up material | 4.7 | 7.5-9.0 | 120-135 |
| LuxaCore | Flowable, core build-up material | 5.6 | 8.8 | 100 |
| Rebilda DC | Flowable, core build-up material | 9.6 | 8.0 | 125 |

*measured with the 3-point bending test according to ISO 4049. An average value of at least six measurements is indicated.
**measured with the penetrometer PNR 10 with a 4 mm flat-head cylinder, 17.6 g. The composite was put in a trough with a diameter of 10 mm and a depth of 20 mm. The penetration was carried out for one second. An average value of three measurements is indicated. The depth of penetration is in this connection measured following ASTM D 1321, as described above.

As is apparent from Examples 1 to 6, the composites according to the invention exhibit a low viscosity with simultaneously high flexural modulus. In contrast to this, the compositions of the state of the art never exhibit both together.

Example 7

For a self-curing composite, the starting paste was prepared from the following components.

| Component | % by weight |
|---|---|
| SR348C | 4.5 |
| DCP | 5.7 |
| HEMA | 1.1 |
| DMA-EMA | 1.4 |
| MDP | 0.4 |
| F360 | 42.7 |
| GM27884 | 14.8 |
| YbF$_3$ | 29.4 |

This starting paste was then divided into equal parts of a base paste and a catalyst paste and the initiators for the self-curing were added:

| Component | % by weight |
|---|---|
| Base paste | |
| Starting paste | 98.9 |
| CC | 0.05 |
| EMBO | 0.05 |
| DABA | 1.00 |
| Catalyst paste | |
| Starting paste | 98.9 |
| BPO | 1.00 |
| BHT | 0.10 |

Both pastes had a depth of penetration of 8.8 mm. After the curing, a flexural modulus of 20 GPa and a flexural strength of 100 MPa were determined.

While specific embodiments of the invention have been described in detail to illustrate the inventive principles, it will be understood that the invention may be embodied otherwise without departing from such principles.

I claim:

1. Low viscosity composites having a depth of penetration of greater than 5 mm measured under ASTM D 1321, which, after curing, have a flexural modulus of at least 18 GPa and a flexural strength of at least 90 MPa comprising
   from 10 to 40% by weight of the polymerizable monomer mixture,
   from 40 to 70% by weight of a first filler comprising aluminum oxides, a first aluminum oxide having a mean particle size of 12-40 μm, and a second aluminum oxide having a mean particle size of 1 to 10 μm,
   from 10 to 45% by weight of at least one additional filler with a mean particle size of 0.5 to 5 μm chosen from the group consisting of glass, glass ceramic, quartz, composite, pyrogenic silicas, titanium dioxide, and zirconium dioxide, and
   from 0.001 to 3% by weight of initiators and additional additives,
   the percentages adding up to 100% by weight.

2. Low viscosity composites according to claim 1, wherein the first filler and optionally also the additional filler are surface-modified.

3. Low viscosity composites according to claim 1, comprising photoinitiators and/or redox systems for the initiation of the polymerization.

* * * * *